US009513546B2

(12) United States Patent
Park et al.

(10) Patent No.: US 9,513,546 B2
(45) Date of Patent: Dec. 6, 2016

(54) MONOMER, HARD MASK COMPOSITION COMPRISING SAID MONOMER, AND METHOD FOR FORMING PATTERN USING SAID HARD MASK COMPOSITION

(71) Applicant: CHEIL INDUSTRIES INC., Gumi-si, Gyeongsangbuk-do (KR)

(72) Inventors: You-Jung Park, Suwon-si (KR); Hea-Jung Kim, Suwon-si (KR); Yo-Choul Park, Suwon-si (KR); Yong-Woon Yoon, Suwon-si (KR); Sung-Jae Lee, Suwon-si (KR); Chul-Ho Lee, Suwon-si (KR); Youn-Jin Cho, Suwon-si (KR)

(73) Assignee: Cheil Industries, Inc., Gumi-Si, Gyeongsangbuk-do (KR)

( * ) Notice: Subject to any disclaimer, the term of this patent is extended or adjusted under 35 U.S.C. 154(b) by 0 days.

(21) Appl. No.: 14/441,294

(22) PCT Filed: Mar. 19, 2013

(86) PCT No.: PCT/KR2013/002239
§ 371 (c)(1),
(2) Date: May 7, 2015

(87) PCT Pub. No.: WO2014/104480
PCT Pub. Date: Jul. 3, 2014

(65) Prior Publication Data
US 2015/0301448 A1    Oct. 22, 2015

(30) Foreign Application Priority Data

Dec. 26, 2012    (KR) .................. 10-2012-0153566

(51) Int. Cl.
*G03F 7/027*    (2006.01)
*G03F 7/16*    (2006.01)
*G03F 7/11*    (2006.01)
*G03F 7/30*    (2006.01)
*G03F 7/36*    (2006.01)
*G03F 7/09*    (2006.01)
*C07C 49/83*    (2006.01)
*C07C 49/798*    (2006.01)
*C07C 49/788*    (2006.01)
*C07C 49/796*    (2006.01)
*C07C 49/835*    (2006.01)
*C07C 49/792*    (2006.01)

(52) U.S. Cl.
CPC ............ *G03F 7/027* (2013.01); *C07C 49/788* (2013.01); *C07C 49/792* (2013.01); *C07C 49/796* (2013.01); *C07C 49/798* (2013.01); *C07C 49/83* (2013.01); *C07C 49/835* (2013.01); *G03F 7/091* (2013.01); *G03F 7/094* (2013.01); *G03F 7/11* (2013.01); *G03F 7/16* (2013.01); *G03F 7/30* (2013.01); *G03F 7/36* (2013.01)

(58) Field of Classification Search
None
See application file for complete search history.

(56) References Cited

FOREIGN PATENT DOCUMENTS

| CN | 1575269 A | 2/2005 |
|---|---|---|
| CN | 101470352 A | 7/2009 |
| CN | 101641390 A | 2/2010 |
| CN | 102566281 A | 7/2012 |
| EP | 1440959 A1 | 7/2004 |
| KR | 10-0826104 B1 | 4/2008 |
| KR | 10-2008-0040777 A | 5/2008 |
| KR | 10-2008-0107208 A | 12/2008 |
| KR | 10-2009-0068444 A | 6/2009 |
| KR | 10-2009-0120827 A | 11/2009 |
| KR | 10-2012-0080139 A | 7/2010 |
| KR | 10-2011-0013819 A | 2/2011 |
| KR | 10-1070548 B1 | 10/2011 |
| KR | 10-2012-0067602 A | 6/2012 |
| KR | 10-2012-0079814 A | 7/2012 |
| KR | 10-2012-0082829 A | 7/2012 |
| KR | 10-2012-0102646 A | 9/2012 |
| TW | 201134799 A1 | 10/2011 |
| TW | 201229672 A1 | 7/2012 |
| WO | WO 2009/128513 A1 | 10/2009 |
| WO | WO 2012/115369 A2 | 8/2012 |

OTHER PUBLICATIONS

Kawai et al (Chemical Abstract—Accession Number: 1953:20939—English abstract for "Synthetic Resins for the Insulation of High-Frequency Waves. I. The Polymerization of Derivatives of 3,6-divinylcarbazole", Nippon Kagaku Zasshi (1952), vol. 73, p. 103-105).*
Ayub et al ("Caluclulation Driven Synthesis of an Excellent Dihydropyrene Negative Photochrome and its Photochemical Properties", Journal of the American Chemical Society, 2011, 133(11), p. 4040-4045).*
Chemical Abstract—Accession No. 2011:241852 (which is English abstract for Ayub et al ("Caluclulation Driven Synthesis of an Excellent Dihydropyrene Negative Photochrome and its Photochemical Properties", Journal of the American Chemical Society, 2011, 133(11), p. 4040-4045)).*
Search Report mailed Aug. 26, 2014 in corresponding Taiwanese Patent Application No. 102113608.
Chinese Search Report dated Dec. 16, 2015 for CN 201380056460X; Park, et al.
Ayub, et al., "Calculation Driven Synthesis of an Excellent Dihydropyrene Negative Photochrome and its Photochemical Properties," J. Am. Chem. Soc., 2011, 133 (11), pp. 4040-4045. (Feb. 23, 2011).
Chinese Search Report dated Sep. 8, 2016 in Corresponding Chinese Patent Application No. 201380056460.

* cited by examiner

Primary Examiner — Sin Lee
(74) Attorney, Agent, or Firm — Lee & Morse, P.C.

(57) ABSTRACT

Disclosed are a monomer for a hardmask composition represented by the Chemical Formula 1, a hardmask composition including the monomer, and a method of forming a pattern using the same.

13 Claims, No Drawings

MONOMER, HARD MASK COMPOSITION COMPRISING SAID MONOMER, AND METHOD FOR FORMING PATTERN USING SAID HARD MASK COMPOSITION

TECHNICAL FIELD

A monomer, a hardmask composition including the monomer, and a method of forming patterns using the hardmask composition are disclosed.

BACKGROUND ART

Recently, the semiconductor industry has developed to an ultra-fine technique having a pattern of several to several tens nanometer size. Such ultrafine technique essentially needs effective lithographic techniques.

The typical lithographic technique includes providing a material layer on a semiconductor substrate; coating a photoresist layer thereon; exposing and developing the same to provide a photoresist pattern; and etching the material layer using the photoresist pattern as a mask.

Nowadays, according to small-sizing the pattern to be formed, it is difficult to provide a fine pattern having an excellent profile by only above-mentioned typical lithographic technique. Accordingly, a layer, called a hardmask layer, may be formed between the material layer and the photoresist layer to provide a fine pattern.

The hardmask layer plays a role of an intermediate layer for transferring the fine pattern of photoresist to the material layer through the selective etching process. Accordingly, the hardmask layer is required to have characteristics such as chemical resistance, and etch resistance or the like to be tolerated during the multiple etching processes.

DISCLOSURE

Technical Problem

One embodiment provides a monomer for a hardmask composition that may reduce a curing temperature since it may be curable at a relatively low temperature and also improve chemical resistance and etch resistance.

Another embodiment provides a hardmask composition including the monomer.

Yet another embodiment provides a method of forming a pattern using the hardmask composition.

Technical Solution

According to one embodiment, a monomer for a hardmask composition represented by the following Chemical Formula 1 is provided:

[Chemical Formula 1]

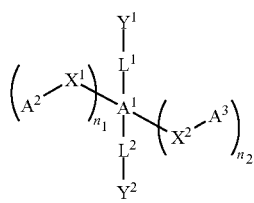

In Chemical Formula 1,
$A^1$ to $A^3$ are each independently a substituted or unsubstituted aliphatic cyclic group or aromatic cyclic group,
$X^1$ and $X^2$ are each independently C=O, $NR^a$, oxygen (O), sulfur (S), $CR^bR^c$, or a combination thereof, wherein $R^a$ to $R^c$ are each independently hydrogen, a substituted or unsubstituted C1 to C10 alkyl group, a hydroxy group, a halogen atom, a halogen-containing group, or a combination thereof, $L^1$ and $L^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, or a combination thereof, $Y^1$ and $Y^2$ are each independently a substituted or unsubstituted C2 to C20 alkenyl group, n1 and n2 are integers of 0≤n1≤10 and 0≤n2≤10, and n1 and n2 are not simultaneously 0.

The $A^1$ to $A^3$ may be each independently a substituted or unsubstituted cyclic group selected from the following Group 1.

[Group 1]

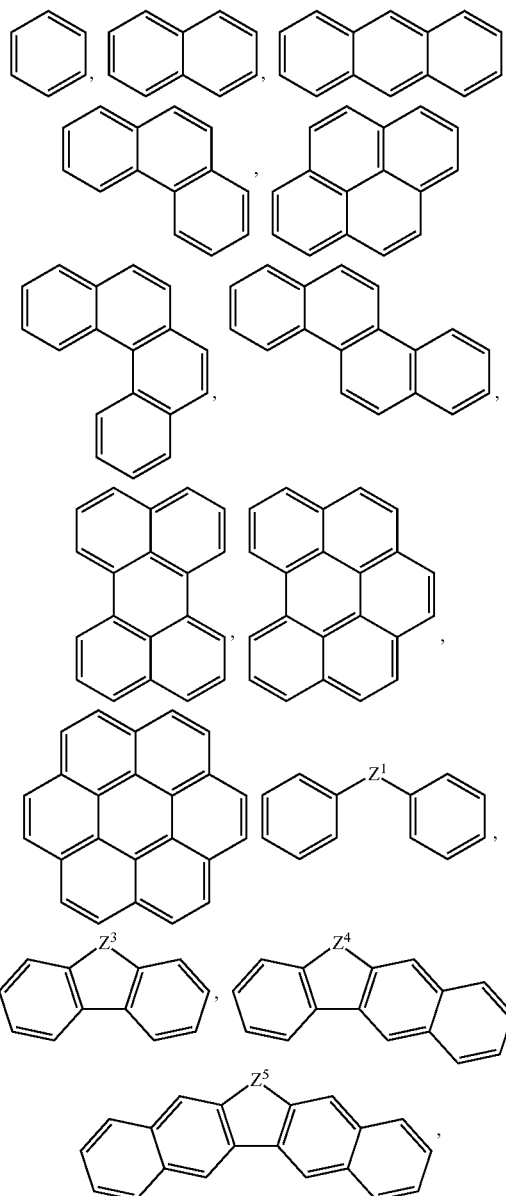

-continued

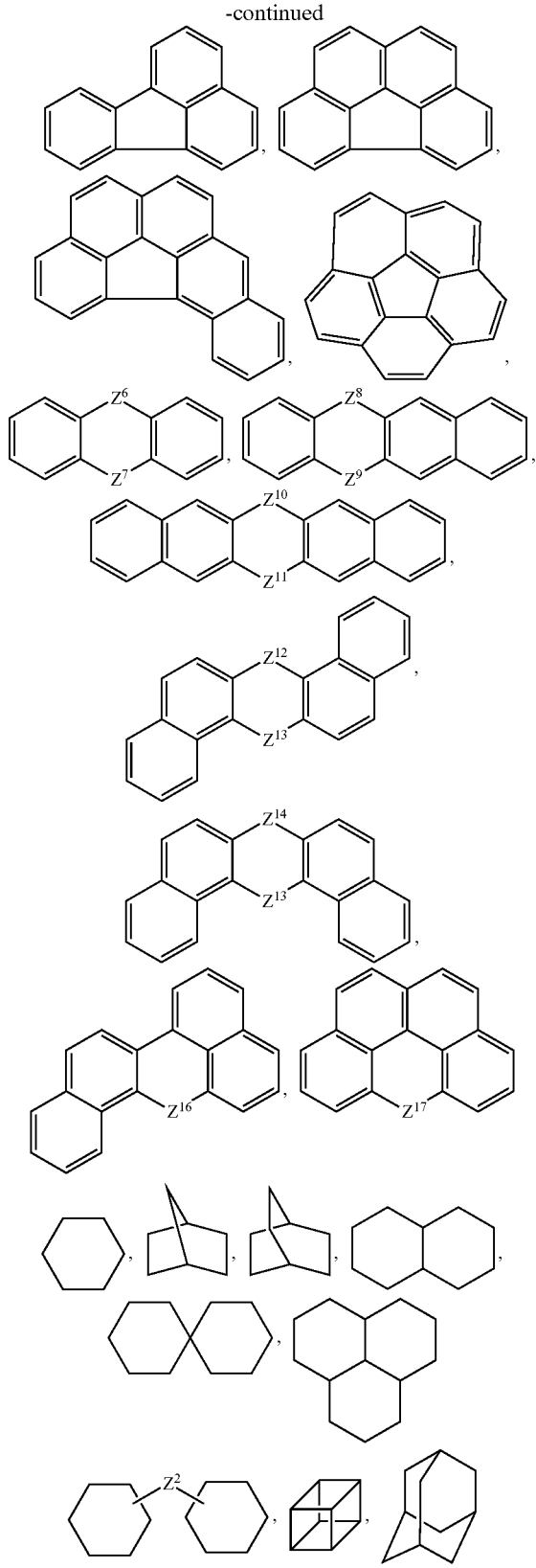

In Group 1,
$Z^1$ and $Z^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR$^a$, oxygen (O), sulfur (S), or a combination thereof, wherein R$^a$ is hydrogen, a substituted or unsubstituted C1 to C10 alkyl group, a halogen atom, or a combination thereof, $Z^3$ to $Z^{17}$ are independently C=O, NR$^a$, oxygen (O), sulfur (S), CR$^b$R$^c$, or a combination thereof, wherein R$^a$ to R$^c$ are each independently hydrogen, a substituted or unsubstituted C1 to C10 alkyl group, a halogen atom, a halogen-containing group, or a combination thereof.

At least one of the $A^1$ to $A^3$ may be a polycyclic aromatic group.

The monomer for a hardmask composition may be represented by one of the following Chemical Formulae 2 to 7.

[Chemical Formula 2]

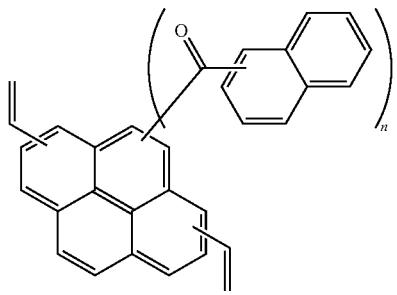

[Chemical Formula 3]

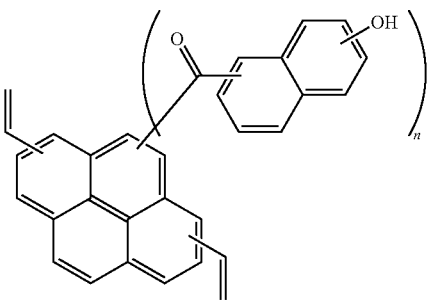

[Chemical Formula 4]

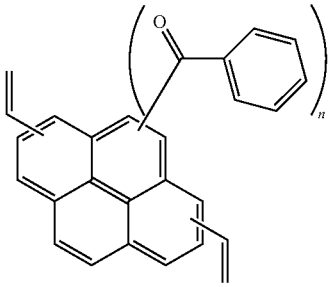

[Chemical Formula 5]

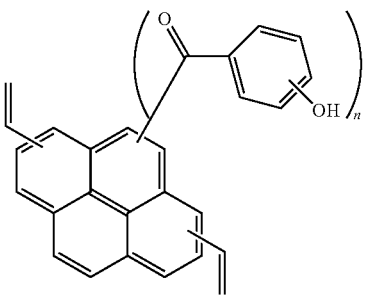

-continued

[Chemical Formula 6]

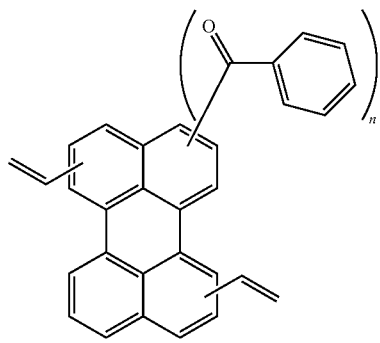

[Chemical Formula 7]

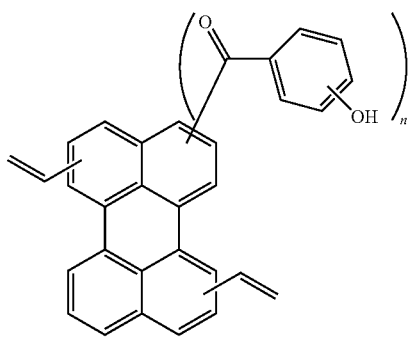

In Chemical Formulae 2 to 7, n is 1 to 4.

The monomer may have a molecular weight of about 200 to about 5,000.

According to another embodiment, a hardmask composition including the monomer and a solvent is provided.

The monomer may be included in an amount of about 0.1 to about 50 wt % based on the total amount of the hardmask composition.

According to yet another embodiment, provided is a method of forming a pattern that includes providing a material layer on a substrate, applying the hardmask composition on the material layer, heat-treating the hardmask composition to provide a hardmask layer, forming a silicon-containing thin layer on the hardmask layer, forming a photoresist layer on the silicon-containing thin layer, forming a photoresist pattern by exposing and developing the photoresist layer, exposing and developing the photoresist layer to form a photoresist pattern, selectively removing the silicon-containing thin layer and the hardmask layer using the photoresist pattern to expose a part of the material layer, and etching an exposed part of the material layer.

The hardmask composition may be applied using a spin-on coating method.

Advantageous Effects

The monomer for a hardmask composition may reduce a curing temperature since it may be curable at a relatively low temperature and also improve chemical resistance and etch resistance.

BEST MODE

Exemplary embodiments of the present invention will hereinafter be described in detail. However, these embodiments are only exemplary and do not limit the present invention. As those skilled in the art would realize, the described embodiments may be modified in various different ways, all without departing from the spirit or scope of the present invention.

As used herein, when a definition is not otherwise provided, the term 'substituted' refers to one substituted with at least a substituent selected from a halogen (F, Br, Cl or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof, instead of hydrogen of a compound.

As used herein, when a definition is not otherwise provided, the prefix "hetero" refers to one including 1 to 3 heteroatoms selected from N, O, S, and P.

Hereinafter, a monomer for a hardmask composition according to one embodiment is described.

The monomer for a hardmask composition according to one embodiment may be represented by the following Chemical Formula 1.

[Chemical Formula 1]

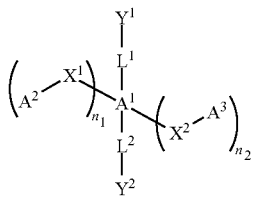

In Chemical Formula 1, $A^1$ to $A^3$ are each independently a substituted or unsubstituted aliphatic cyclic group or aromatic cyclic group, $X^1$ and $X^2$ are each independently C=O, $NR^a$, oxygen (O), sulfur (S), $CR^bR^c$, or a combination thereof, wherein $R^a$ to $R^c$ are each independently hydrogen, a substituted or unsubstituted C1 to C10 alkyl group, a hydroxy group, a halogen atom, a halogen-containing group, or a combination thereof, $L^1$ and $L^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, or a combination thereof, $Y^1$ and $Y^2$ are each independently a substituted or unsubstituted C2 to C20 alkenyl group, n1 and n2 are integers of 0≤n1≤10 and 0≤n2≤10, and n1 and n2 are not simultaneously 0.

The monomer includes an aliphatic cyclic group or an aromatic cyclic group having one or more than two cycles in its core and also, alkenyl groups $Y^1$ and $Y^2$ directly or indirectly linked to the aliphatic cyclic group or the aromatic cyclic group. The alkenyl group may increase cross-linking of the monomer during the curing and thus, cross-linking density thereof. Accordingly, the monomer is cured at a relatively low temperature and may form a thin layer having excellent chemical and etching resistances and high uniformity.

In addition, a substituent connected to the core may include an aliphatic cyclic group or an aromatic cyclic group and may be used to regulate property of the thin layer.

Furthermore, the aliphatic cyclic group or the aromatic cyclic group included in the substituent may include a functional group such as a hydroxy group, which may improve solubility and thus, effectively form the thin layer using a spin-on coating method. When the thin layer is spin-on coated on a lower layer having a predetermined pattern, gap-filling among the patterns and flatness characteristics may be improved.

The $A^1$ to $A^3$ may be each independently substituted or unsubstituted cyclic group selected from the following Group 1.

[Group 1]

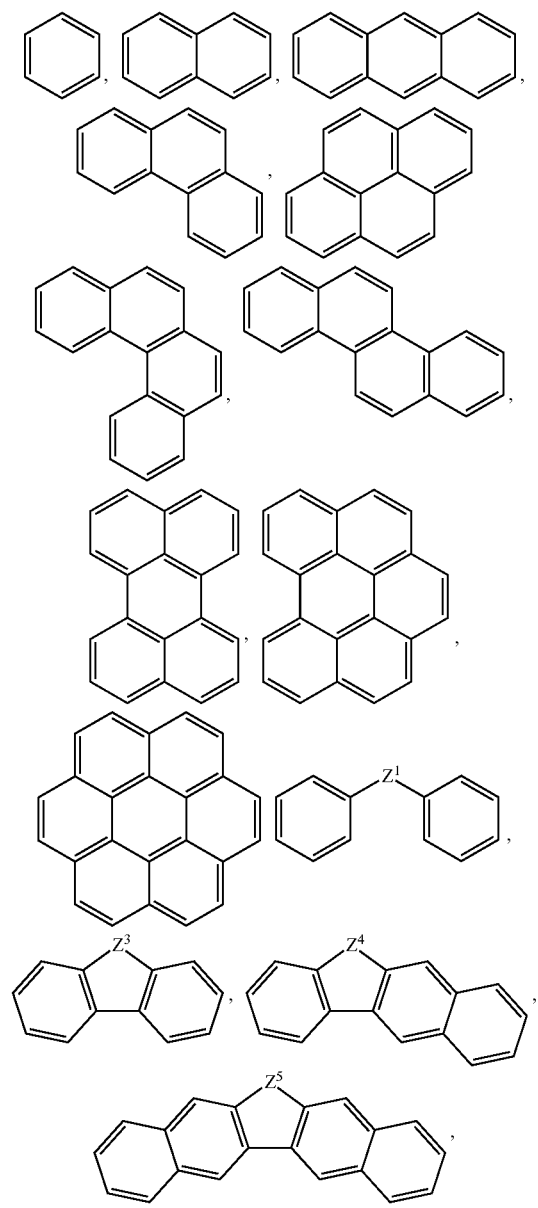

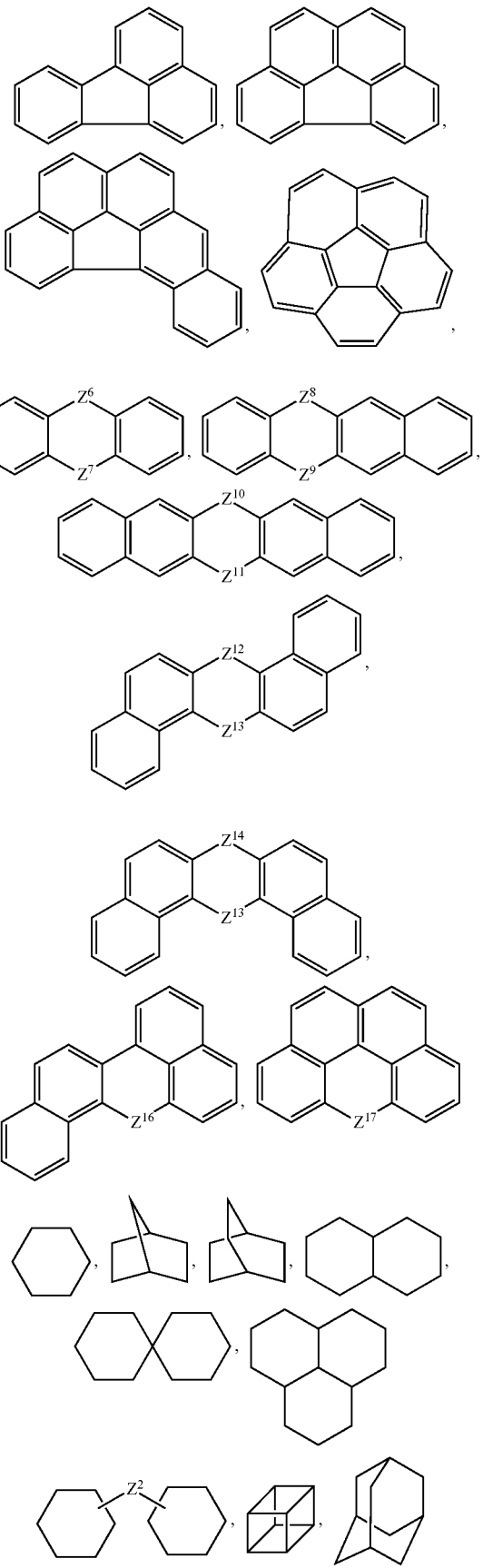

In Group 1, $Z^1$ and $Z^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, $NR^a$, oxygen (O), sulfur (S), or a combination thereof, wherein $R^a$ is hydrogen, a substituted or unsubstituted C1 to C10 alkyl group, a halogen atom, or a combination thereof, $Z^3$ to $Z^{17}$ are independently C=O, $NR^a$, oxygen (O), sulfur (S), $CR^bR^c$, or a combination thereof, wherein $R^a$ to $R^c$ are each independently hydrogen, a substituted or unsubstituted C1 to C10 alkyl group, a halogen atom, a halogen-containing group, or a combination thereof.

In Group 1, linking positions of each ring are not particularly limited, and each ring may be substituted or unsubstituted. When the ring listed in the Group 1 is a substituted ring, it may be for example substituted with a C1 to C20 alkyl group, a halogen atom, a hydroxy group, and the like, without limitation.

At least one of $A^1$ to $A^3$ may be a substituted or unsubstituted aromatic group, for example a benzene group, a naphthalene group, a biphenyl group, a pyrene group, a perylene group, a benzoperylene group, a coronene group, or a combination thereof.

At least one of $A^1$ to $A^3$ may be a polycyclic aromatic group, for example a pyrene group, a perylene group, a benzoperylene group, a coronene group, or a combination thereof.

At least one of $A^2$ and $A^3$ may be an aromatic group substituted with a hydroxy group.

The monomer may be represented by one of the following Chemical Formulae 2 to 7.

[Chemical Formula 2]

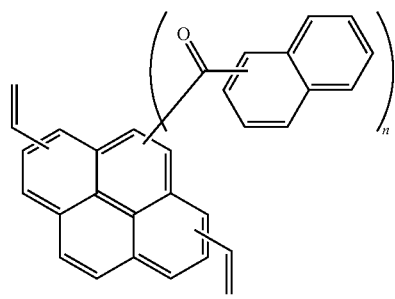

[Chemical Formula 3]

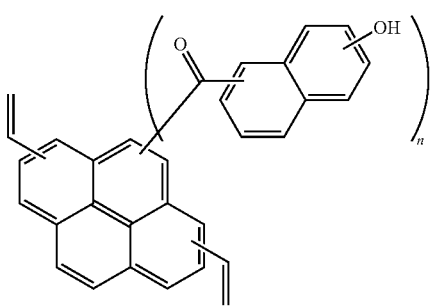

[Chemical Formula 4]

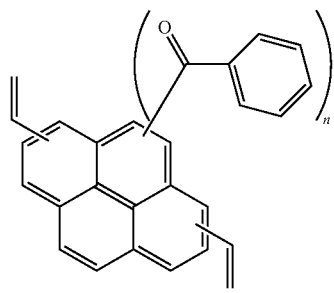

[Chemical Formula 5]

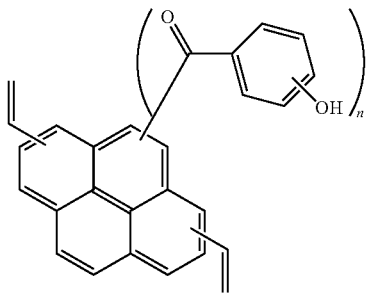

[Chemical Formula 6]

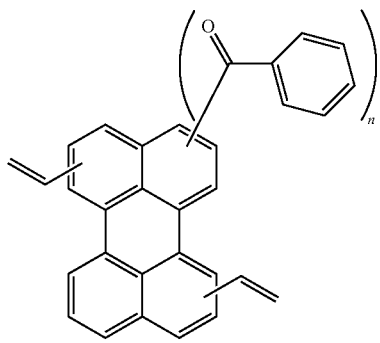

[Chemical Formula 7]

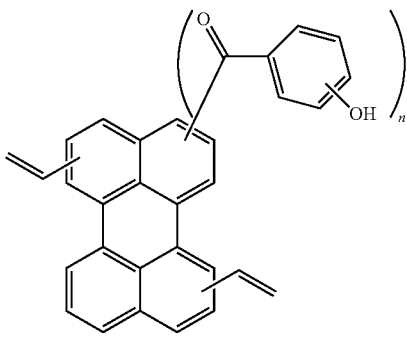

In Chemical Formulae 2 to 7, n is 1 to 4.

The monomer may have a molecular weight of about 200 to about 5000. When the monomer has a molecular weight within the above range, solubility of the monomer having a high carbon content in a solvent may be improved and an improved thin layer may be obtained through spin-on coating.

Hereinafter, a hardmask composition according to one embodiment is described.

The hardmask composition according to one embodiment includes the monomer and a solvent.

The monomer is the same as described above, and one kind of monomer may be used singularly and two kinds of monomers may be mixed.

The solvent may be anyone having sufficient dissolubility or dispersion for the monomer and may be, for example at least one selected from propyleneglycol, propyleneglycol diacetate, methoxy propanediol, diethyleneglycol, diethyleneglycol butylether, tri(ethyleneglycol)monomethylether, propyleneglycol monomethylether, propyleneglycol monomethylether acetate, cyclohexanone, ethyllactate, gamma-butyrolactone, methylpyrrolidone, acetylacetone, and ethyl 3-ethoxypropinate.

The monomer may be included in an amount of about 0.1 to about 50 wt % based on the total amount of the hardmask composition. When the monomer is included in the above range, a thickness of a coated thin layer may be obtained.

The hardmask composition may further include a surfactant.

The surfactant may include, for example, an alkylbenzene sulfonate salt, an alkyl pyridinium salt, polyethylene glycol, or a quaternary ammonium salt, but is not limited thereto.

The surfactant may be included in an amount of about 0.001 to 3 parts by weight based on 100 parts by weight of the hardmask composition. Within the amount range, the solubility and the cross-linking may be secured while not changing the optical properties of the hardmask composition.

Hereafter, a method for forming patterns by using the hardmask composition is described.

A method of forming a pattern according to one embodiment substrate includes providing a material layer on a substrate, applying a hardmask composition including the monomer and a solvent on the material layer, heat-treating the hardmask composition to provide a hardmask layer, forming a silicon-containing thin layer on the hardmask layer, forming a photoresist layer on the silicon-containing thin layer, forming a photoresist pattern by exposing and developing the photoresist layer, selectively removing the silicon-containing thin layer and the hardmask layer by using the photoresist pattern and exposing a part of the material layer, and etching the exposed part of the material layer.

The substrate may be, for example, a silicon wafer, a glass substrate, or a polymer substrate.

The material layer is a material to be finally patterned, for example a metal layer such as an aluminum layer and a copper layer, a semiconductor layer such as a silicon layer, or an insulation layer such as a silicon oxide layer and a silicon nitride layer. The material layer may be formed through a method such as a chemical vapor deposition (CVD) process.

The hardmask composition may be applied by spin-on coating in a form of a solution. Herein, the hardmask composition may be applied at a thickness, for example about 50 Å to 50,000 Å.

The heat-treating the hardmask composition may be performed, for example about 100 to 500° C. for about 10 seconds to 10 minutes. During heat-treating, the monomer may cause a self cross-linking and/or mutual cross-linking reaction.

The silicon-containing thin layer may be made of, for example silicon nitride or silicon oxide.

A bottom anti-reflective coating (BARC) may be formed on the silicon-containing thin layer.

The exposure of the photoresist layer may be performed using for example ArF, KrF, or EUV. Also, after the exposure, heat-treating may be performed at about 100 to 500° C.

The etching process of the exposed part of the material layer may be performed through a dry etching process using an etching gas, and the etching gas may be, for example $CHF_3$, $CF_4$, $Cl_2$, $BCl_3$, and a mixed gas thereof.

The etched material layer may be formed in a plurality of pattern, and the plurality of pattern may be a metal pattern, a semiconductor pattern, an insulation pattern, and the like, for example diverse pattern of a semiconductor integrated circuit device.

Mode for Invention

Hereinafter, the present invention is illustrated in more detail with reference to examples. However, they are exemplary embodiments of the present invention and are not limiting.

Synthesis of Monomer

SYNTHESIS EXAMPLE 1

2.54 g (0.01 mol) of 2,7-divinylpyrene, 3.12 g (0.02 mol) of 4-hydroxybenzoyl chloride, and 50 ml of 1,1-dichloroethane were put in a flask and agitated for one hour under a nitrogen atmosphere, and 2.93 g (0.022 mol) of $AlCl_3$ was slowly added thereto. The mixture was agitated at room temperature. Next, 50 ml of deionized water was added to the agitated mixture to complete the reaction after performing gel permeation chromatography (GPC) to check if the starting materials were all removed (12 hr, RT). Then, an organic layer produced therein was extracted with 50 ml of ethylacetate and then, twice cleaned with 30 ml of deionized water and concentrated under a reduced pressure, obtaining a compound represented by the following Chemical Formula 8.

[Chemical Formula 8]

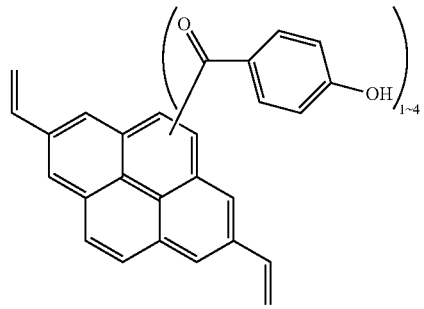

The compound had a yield of 81% and an average molecular weight of 510.

SYNTHESIS EXAMPLE 2

2.54 g (0.01 mol) of 2,7-divinylpyrene, 5.72 g (0.03 mol) of 2-naphthylchloride, and 50 ml of dichloroethane were put in a flask and agitated for 1 hour under a nitrogen atmosphere, and 4.39 g (0.033 mol) of $AlCl_3$ was slowly added thereto. The mixture was agitated at room temperature again. Next, 50 ml of deionized water was added to the agitated mixture to complete the reaction after performing gel permeation chromatography (GPC) to check if the starting materials were all removed (18 hr, RT). Then, an organic layer produced therein was extracted with 50 ml of ethylacetate and then, twice cleaned with 30 ml of deionized water and concentrated under a reduced pressure, obtaining a compound represented by the following Chemical Formula 9.

[Chemical Formula 9]

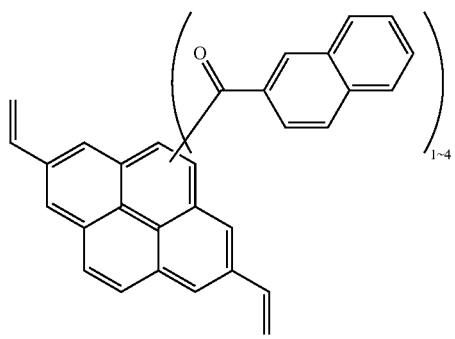

The compound had a yield of 73% and an average molecular weight of 486.

SYNTHESIS EXAMPLE 3

3.04 g (0.01 mol) of 1,7-divinylperylene, 4.68 g (0.03 mol) of 4-hydroxy benzoylchloride, and 50 ml of 1,1-dichloroethane were put in a flask and agitated for 1 hour under a nitrogen atmosphere, and 4.39 g (0.033 mol) of $AlCl_3$ was slowly added thereto. The mixture was agitated at room temperature again and then, heated to 80° C. and refluxed. Next, 50 ml of deionized water was added to the refluxed mixture to complete the reaction after performing gel permeation chromatography (GPC) to check if the starting materials were all removed (10 hr and 80° C.). Then, an organic layer produced therein was extracted using a mixed solvent of 50 ml of ethylacetate and 30 ml of tetrahydrofuran (THF) and then, twice cleaned with 30 ml of deionized water and concentrated under a reduced pressure, obtaining a compound represented by the following Chemical Formula 10.

[Chemical Formula 10]

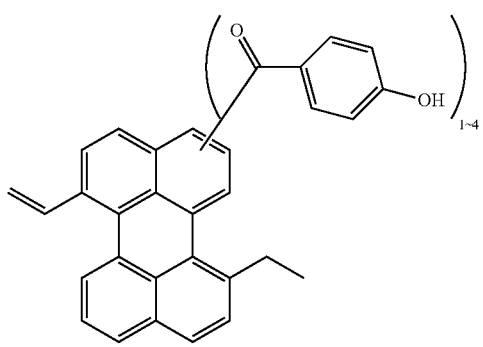

The compound had a yield of 48% and an average molecular weight of 605.

COMPARATIVE SYNTHESIS EXAMPLE 1

A compound represented by the following Chemical Formula 11 was synthesized according to the same method as Synthesis Example 1 except for using pyrene instead of 2,7-divinylpyrene.

[Chemical Formula 11]

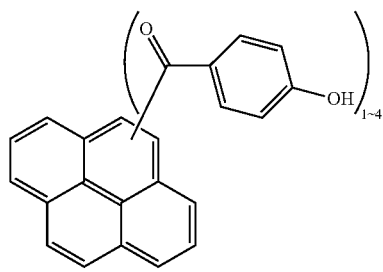

The compound had a yield of 68% and an average molecular weight of 470.

COMPARATIVE SYNTHESIS EXAMPLE 2

A compound represented by the following Chemical Formula 12 was synthesized according to the same method as Example 2 except for using pyrene instead of 2,7-divinylpyrene.

[Chemical Formula 12]

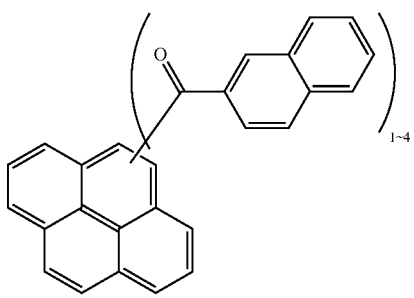

The compound had a yield of 81% and an average molecular weight of 433.

COMPARATIVE SYNTHESIS EXAMPLE 3

A compound represented by the following Chemical Formula 13 was synthesized according to the same method as Example 3 except for using perylene instead of 1,7-divinylperylene.

[Chemical Formula 13]

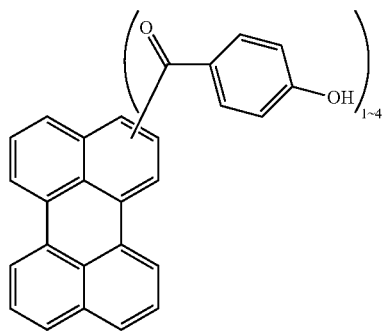

The compound had a yield of 79% and an average molecular weight of 553.

Preparation of Hardmask Composition

EXAMPLE 1

A hardmask composition was prepared by completely dissolving 1 g of the compound according to Synthesis Example 1 in 9 g of propylene glycol monomethyl ether acetate (PGMEA).

EXAMPLE 2

A hardmask composition was prepared by completely dissolving 1 g of the compound according to Synthesis Example 2 in 9 g of propylene glycol monomethyl ether acetate (PGMEA).

EXAMPLE 3

A hardmask composition was prepared by completely dissolving 1 g of the compound according to Synthesis Example 3 in 9 g of propylene glycol monomethyl ether acetate (PGMEA).

COMPARATIVE EXAMPLE 1

A hardmask composition was prepared by completely dissolving 1 g of the compound according to Comparative Synthesis Example 1 in 9 g of propylene glycol monomethyl ether acetate (PGMEA).

COMPARATIVE EXAMPLE 2

A hardmask composition was prepared by completely dissolving 1 g of the compound according to Comparative Synthesis Example 2 in 9 g of propylene glycol monomethyl ether acetate (PGMEA).

COMPARATIVE EXAMPLE 3

A hardmask composition was prepared by completely dissolving 1 g of the compound according to Comparative Synthesis Example 3 in 9 g of propylene glycol monomethyl ether acetate (PGMEA).

Evaluation

Evaluation 1: Chemical Resistance

The hardmask compositions according to Examples 1 to 3 and Comparative Examples 1 to 3 were respectively coated on a silicon wafer and heated by every 20° C. from 200° C. to 300° C. on a plate for 60 second, forming a 2800 Å-thick layer. The silicon wafer coated with the hardmask composition was half dipped in a KrF thinner and examined with bare eyes and then, measured regarding thin layer thickness using Ellipsometer (J.A. Woollam Co. inc.), an equipment for measuring thickness of a thin layer.

Table 1 provides results of the hardmask compositions according to Examples 1 to 3, while Table 2 provides results of the hardmask compositions according to Comparative Examples 1 to 3.

TABLE 1

| | Example 1 | | | Example 2 | | | Example 3 | | |
|---|---|---|---|---|---|---|---|---|---|
| Temperature (° C.) | Before dipping (Å) | After dipping (Å) | Decrease ratio (%) | Before dipping (Å) | After dipping (Å) | Decrease ratio (%) | Before dipping (Å) | After dipping (Å) | Decrease ratio (%) |
| 200 | 2894 | 2554 | 11.75 | 2831 | 2531 | 10.60 | 2816 | 2480 | 11.93 |
| 220 | 2865 | 2739 | 4.40 | 2824 | 2708 | 4.11 | 2814 | 2762 | 1.85 |
| 240 | 2845 | 2828 | 0.60 | 2793 | 2777 | 0.57 | 2795 | 2784 | 0.39 |
| 260 | 2844 | 2841 | 0.11 | 2794 | 2796 | −0.07 | 2805 | 2826 | −0.75 |
| 280 | 2815 | 2833 | −0.64 | 2804 | 2805 | −0.04 | 2780 | 2785 | −0.18 |
| 300 | 2836 | 2836 | 0.00 | 2781 | 2772 | 0.32 | 2774 | 2776 | −0.07 |
| 400 | 2872 | 2566 | 0.23 | 2553 | 2559 | −0.24 | 2554 | 2558 | −0.16 |

TABLE 2

| | Comparative Example 1 | | | Comparative Example 2 | | | Comparative Example 3 | | |
|---|---|---|---|---|---|---|---|---|---|
| Temperature (° C.) | Before dipping (Å) | After dipping (Å) | Decrease ratio (%) | Before dipping (Å) | After dipping (Å) | Decrease ratio (%) | Before dipping (Å) | After dipping (Å) | Decrease ratio (%) |
| 200 | 2850 | 1201 | 57.86 | 2810 | 1265 | 54.98 | 2846 | 1211 | 57.45 |
| 220 | 2843 | 1298 | 54.34 | 2804 | 1270 | 54.71 | 2840 | 1230 | 56.69 |
| 240 | 2828 | 1695 | 40.06 | 2791 | 1779 | 36.26 | 2834 | 1889 | 33.35 |
| 260 | 2825 | 2561 | 9.35 | 2801 | 2531 | 9.64 | 2828 | 2497 | 11.70 |
| 280 | 2822 | 2818 | 0.14 | 2796 | 2701 | 3.40 | 2805 | 2804 | 0.04 |
| 300 | 2810 | 2805 | 0.18 | 2770 | 2775 | −0.18 | 2828 | 2806 | 0.78 |
| 400 | 2593 | 2593 | 0.00 | 2578 | 2583 | −0.19 | 2578 | 2579 | −0.04 |

Referring to Tables 1 and 2, the hardmask compositions according to Examples 1 to 3 were sufficiently cured at about 240° C. and had almost no thickness change due to the KrF thinner, while the hardmask compositions according to Comparative Examples 1 to 3 were less cured at about 240° C. and had a large thickness change but were sufficiently cured at about 400° C.

Accordingly, the hardmask compositions according to Examples 1 to 3 were cured at a lower temperature than the ones according to Comparative Examples 1 to 3 and thus, had excellent chemical resistance at a relatively low temperature of about 240° C.

Evaluation 2: Etching Resistance

The hardmask compositions according to Examples 1 to 3 and Comparative Examples 1 to 3 were respectively spin-on coated on a silicon wafer and then, heat-treated at 240° C. for 1 minute on a hot plate to provide thin layers. The thin layers were measured regarding thickness by a thin layer thickness gauge manufactured by K-MAC.

Then, the thin layers were dry etched for 60 seconds using $N_2/O_2$ mixed gas and measured regarding thickness. In addition, the thin layers were dry-etched for 100 seconds using $CF_x$ gas and then, measured regarding thickness.

Then, the bulk etching rates (BER) of the thin layers were calculated according to the following Equation 3 using thicknesses of each thin layer before and after the dry etching and etching time thereof.

(Thickness of initial thin layer−Thickness of thin layer after etching)/Etching time (Å/s)   [Equation 3]

The results are provided in Table 3.

TABLE 3

| | Etching rate (Å/s) | | | |
|---|---|---|---|---|
| | $N_2/O_2$ | | $CF_x$ | |
| | 240° C. | 400° C. | 240° C. | 400° C. |
| Example 1 | 19.4 | 18.2 | 27.2 | 23.5 |
| Example 2 | 20.1 | 18.9 | 26.9 | 24.5 |
| Example 3 | 19.1 | 17.8 | 29.9 | 24 |
| Comparative Example 1 | 20.9 | 18.6 | 28 | 24.9 |
| Comparative Example 2 | 21.7 | 19.4 | 28.5 | 25 |
| Comparative Example 3 | 21.3 | 18.5 | 31.3 | 24.5 |

Referring to Table 3, the thin layers respectively formed of the hardmask compositions according to Examples 1 to 3 had sufficient etching resistance against etching gas and thus, a lower etching rate compared with the thin layers formed of the hardmask compositions according to Comparative Examples 1 to 3.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A cross-linkable monomer for a hardmask composition, the monomer being represented by the following Chemical Formula 1:

[Chemical Formula 1]

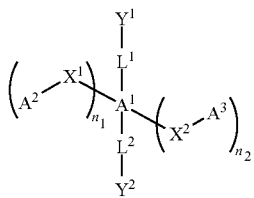

wherein, in Chemical Formula 1,
$A^2$ to $A^3$ are each independently a substituted or unsubstituted aliphatic cyclic group or aromatic cyclic group, and
$A^1$ is a substituted or unsubstituted aliphatic cyclic group or aromatic cyclic group selected from the following Group 1:

[Group 1]

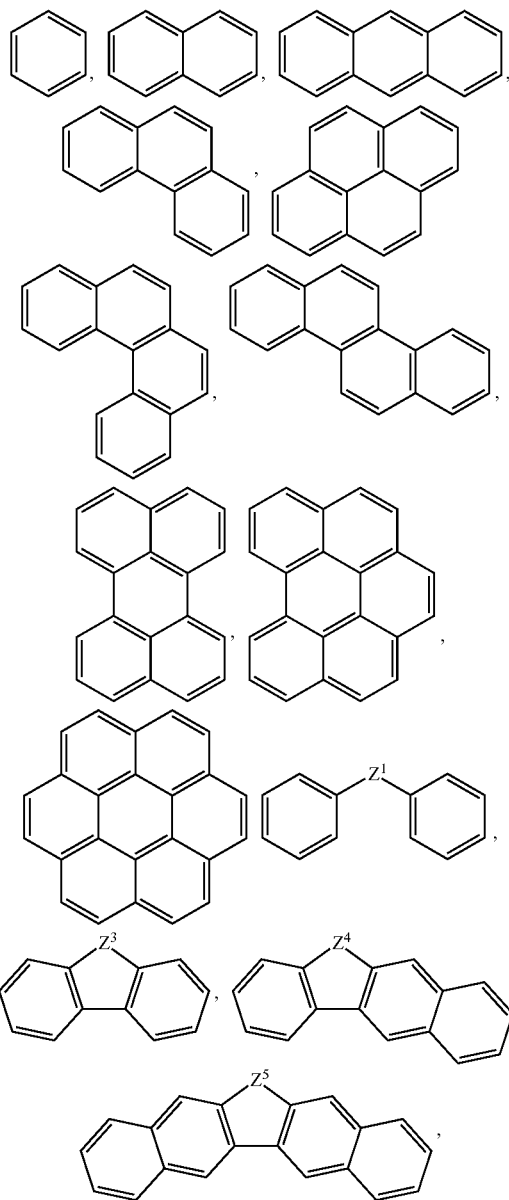

-continued

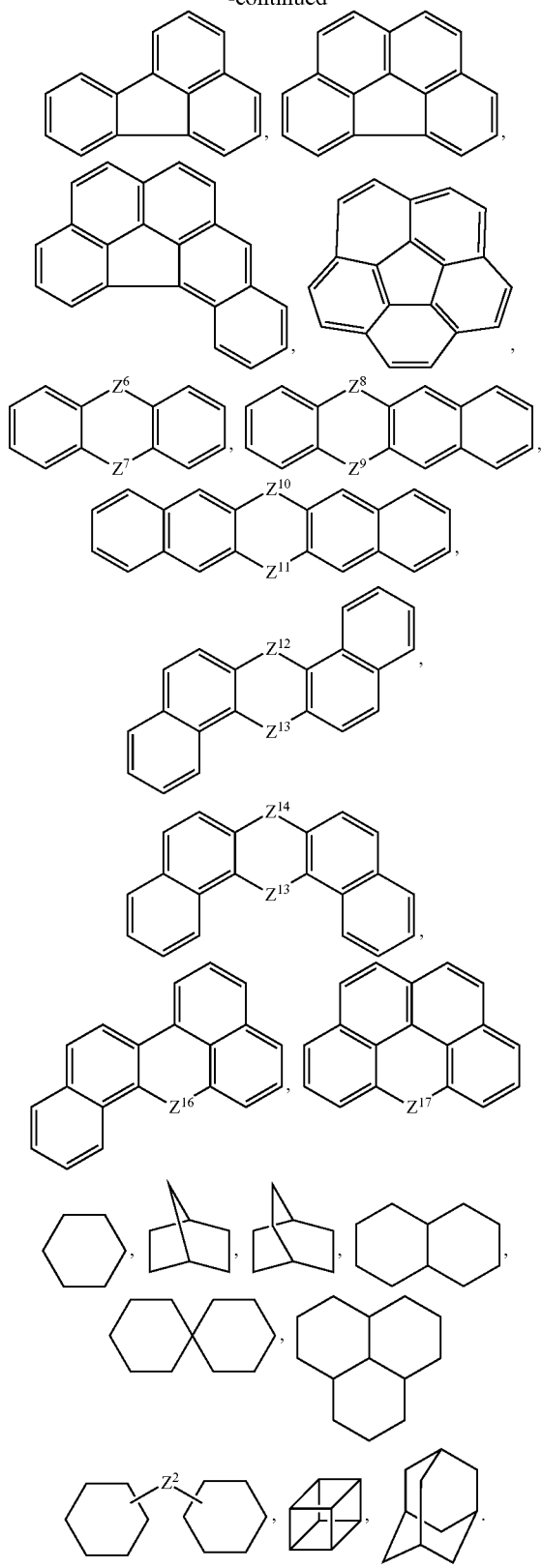

wherein, in Group 1,
Z¹ and Z² are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR$^a$, oxygen (O), sulfur (S), or a combination thereof, wherein R$^a$ is hydrogen, a substituted or unsubstituted C1 to C10 alkyl group, a halogen atom, or a combination thereof, and Z³ to Z¹⁷ are independently C=O, NR$^a$, oxygen (O), sulfur (S), CR$^b$R$^c$, or a combination thereof, wherein R$^a$ to R$^c$ are each independently hydrogen, a substituted or unsubstituted C1 to C10 alkyl group, a halogen atom, a halogen-containing group, or a combination thereof, X¹ and X² are each independently C=O, NR$^a$, oxygen (O), sulfur (S), CR$^b$R$^c$, or a combination thereof, wherein R$^a$ to R$^c$ are each independently hydrogen, a substituted or unsubstituted C1 to C10 alkyl group, a hydroxy group, a halogen atom, a halogen-containing group, or a combination thereof, at least one of X¹ or X² being C=O, L¹ and L² are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, or a combination thereof, Y¹ and Y² are each independently a substituted or unsubstituted C2 to C20 alkenyl group, n1 and n2 are integers of 0≤n1≤10 and 0≤n2≤10, and n1 and n2 are not simultaneously 0.

2. The monomer of claim 1, wherein A² to A³ are each independently a substituted or unsubstituted cyclic group selected from the following Group 1:

[Group 1]

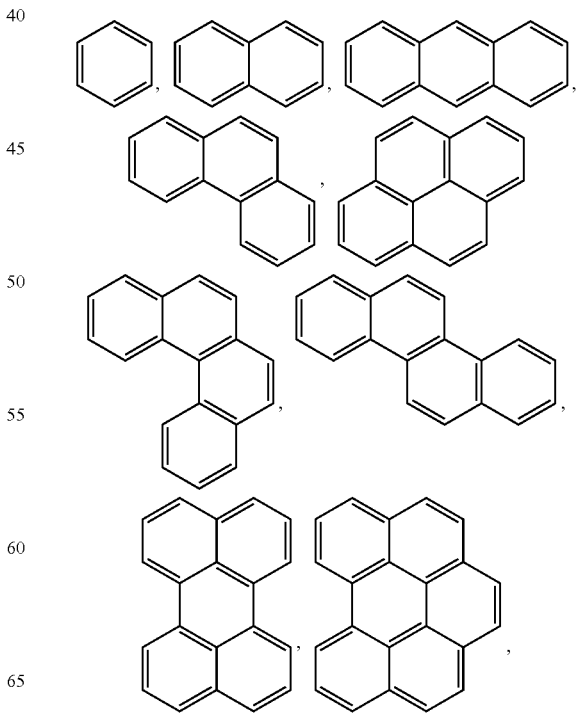

-continued

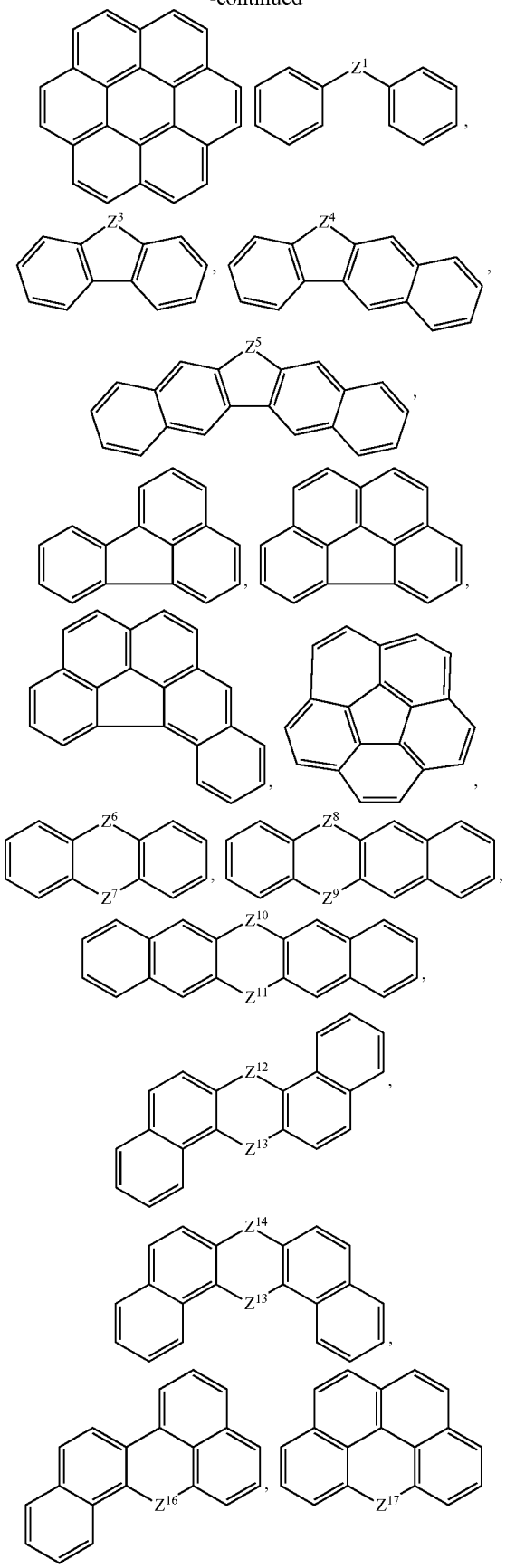

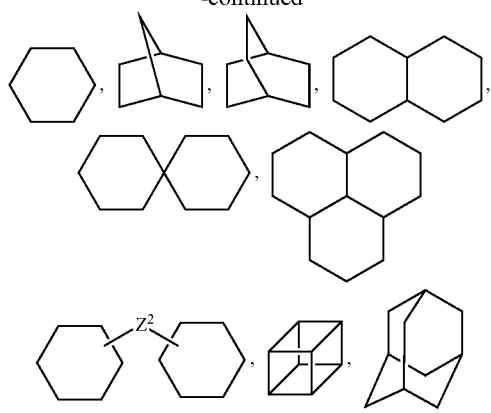

wherein, in Group 1,

Z¹ and Z² are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR$^a$, oxygen (O), sulfur (S), or a combination thereof, wherein R$^a$ is hydrogen, a substituted or unsubstituted C1 to C10 alkyl group, a halogen atom, or a combination thereof, and Z³ to Z¹⁷ are independently C=O, NR$^a$, oxygen (O), sulfur (S), CR$^b$R$^c$, or a combination thereof, wherein R$^a$ to R$^c$ are each independently hydrogen, a substituted or unsubstituted C1 to C10 alkyl group, a halogen atom, a halogen-containing group, or a combination thereof.

3. The monomer of claim 1, wherein at least one of A¹ to A³ is a polycyclic aromatic group.

4. The monomer of claim 1, wherein the monomer is represented by one of the following Chemical Formulae 2 to 7:

[Chemical Formula 2]

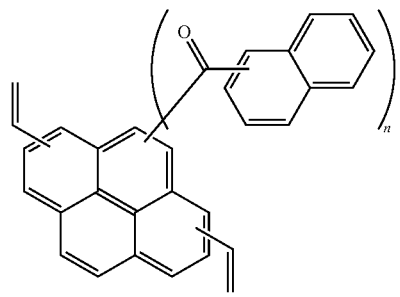

[Chemical Formula 3]

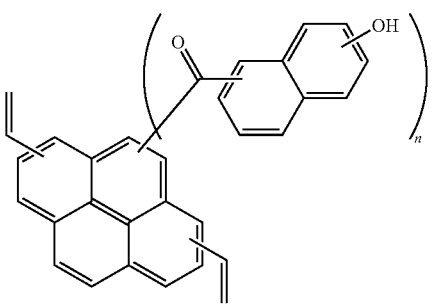

[Chemical Formula 4]
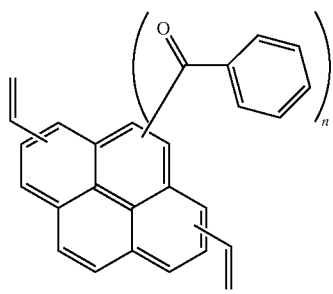

[Chemical Formula 5]
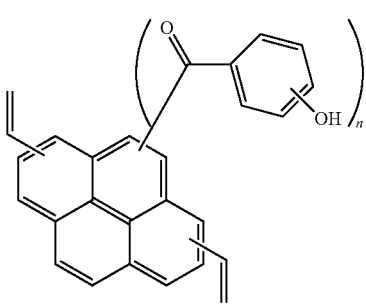

[Chemical Formula 6]
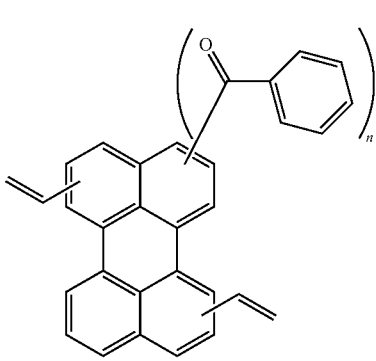

[Chemical Formula 7]
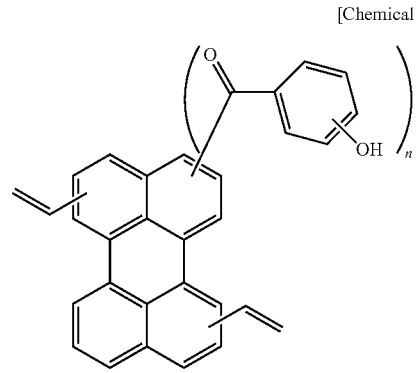

wherein in Chemical Formulae 2 to 7, n is 1 to 4.

5. The monomer of claim 1, wherein the monomer has a molecular weight of about 200 to about 5,000.

6. A hardmask composition, comprising
a cross-linkable monomer represented by the following Chemical Formula 1, and a solvent:

[Chemical Formula 1]
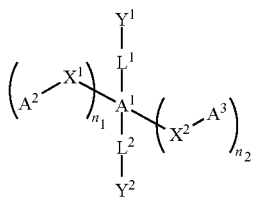

wherein, in Chemical Formula 1, $A^1$ to $A^3$ are each independently a substituted or unsubstituted aliphatic cyclic group or aromatic cyclic group, $X^1$ and $X^2$ are each independently C=O, $NR^a$, oxygen (O), sulfur (S), $CR^bR^c$, or a combination thereof, wherein $R^a$ to $R^c$ are each independently hydrogen, a substituted or unsubstituted C1 to C10 alkyl group, a hydroxy group, a halogen atom, a halogen-containing group, or a combination thereof, $L^1$ and $L^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, or a combination thereof, $Y^1$ and $Y^2$ are each independently a substituted or unsubstituted C2 to C20 alkenyl group, n1 and n2 are integers of $0 \leq n1 \leq 10$ and $0 \leq n2 \leq 10$, and n1 and n2 are not simultaneously 0.

7. The hardmask composition of claim 6, wherein the $A^1$ to $A^3$ are each independently a substituted or unsubstituted cyclic group selected from the following Group 1:

[Group 1]
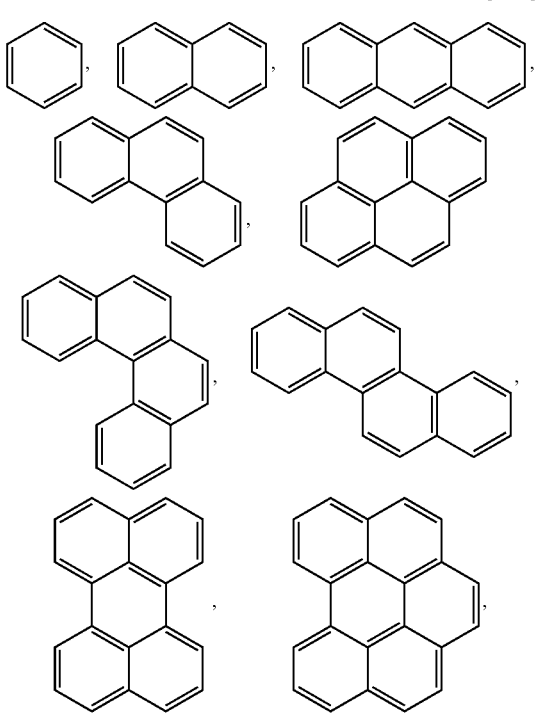

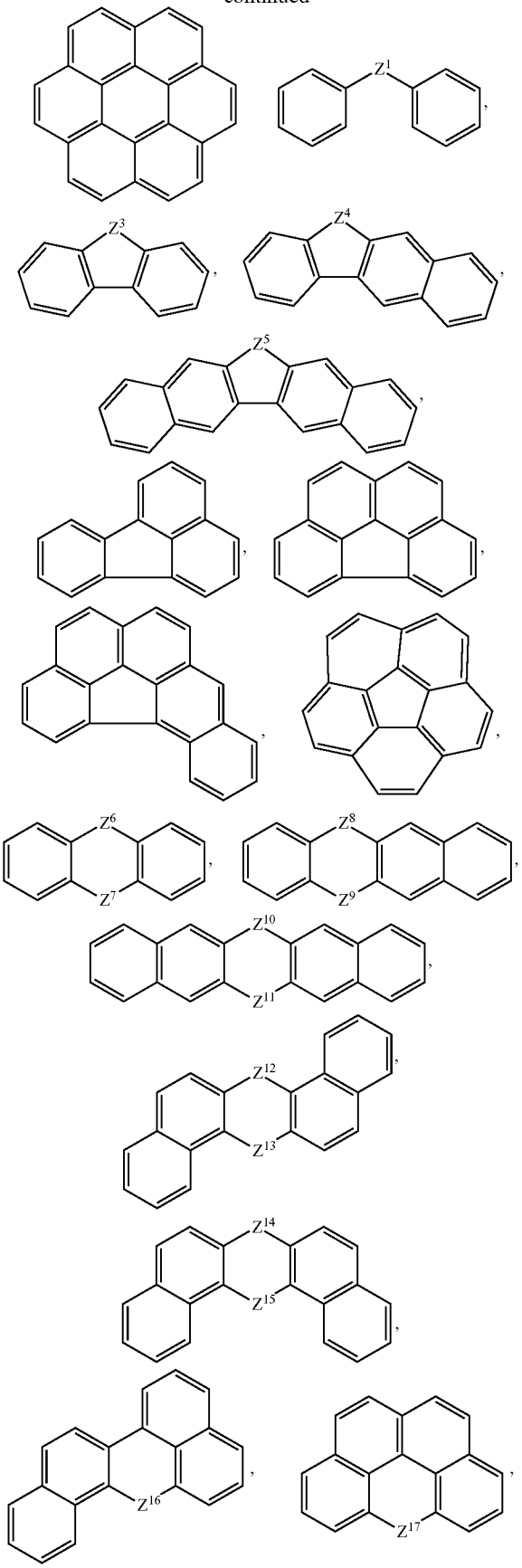

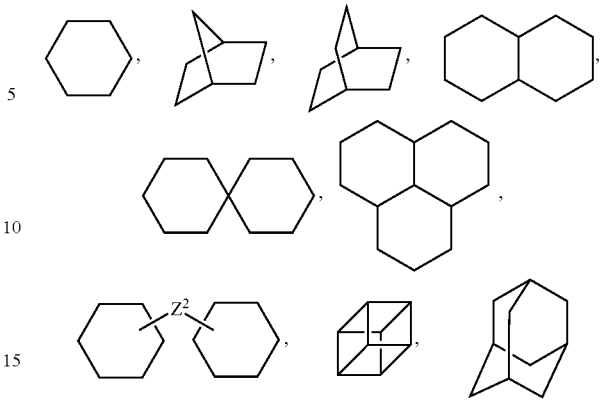

wherein, in Group 1,

Z$^1$ and Z$^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, NR$^a$, oxygen (O), sulfur (S), or a combination thereof, wherein R$^a$ is hydrogen, a substituted or unsubstituted C1 to C10 alkyl group, a halogen atom, or a combination thereof, Z$^3$ to Z$^{17}$ are independently C=O, NR$^a$, oxygen (O), sulfur (S), CR$^b$R$^c$, or a combination thereof, wherein R$^a$ to R$^c$ are each independently hydrogen, a substituted or unsubstituted C1 to C10 alkyl group, a halogen atom, a halogen-containing group, or a combination thereof.

8. The hardmask composition of claim 6, wherein at least one of A$^1$ to A$^3$ is a polycyclic aromatic group.

9. The hardmask composition of claim 6, wherein the monomer is represented by one of the following Chemical Formulae 2 to 7:

[Chemical Formula 2]

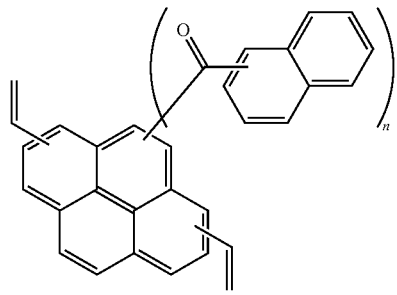

[Chemical Formula 3]

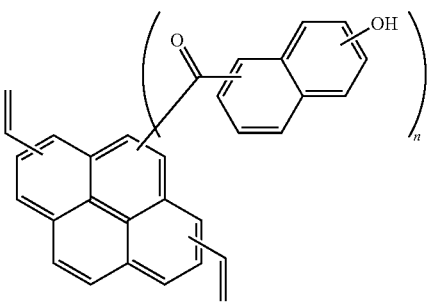

-continued

[Chemical Formula 4]

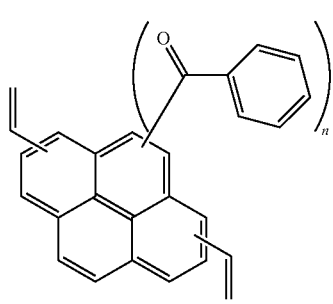

[Chemical Formula 5]

[Chemical Formula 6]

[Chemical Formula 7]

wherein in Chemical Formulae 2 to 7, n is 1 to 4.

10. The hardmask composition of claim 6, wherein the monomer has a molecular weight of 200 to 5,000.

11. The hardmask composition of claim 6, wherein the monomer is included in an amount of 0.1 to about 50 wt % based on the total amount of the hardmask composition.

12. A method of forming a pattern, comprising:
providing a material layer on a substrate,
applying a hardmask composition on the material layer,
heat-treating the hardmask composition to provide a hardmask layer,
forming a silicon-containing thin layer on the hardmask layer,
forming a photoresist layer on the silicon-containing thin layer,
forming a photoresist pattern by exposing and developing the photoresist layer,
selectively removing the silicon-containing thin layer and the hardmask layer using the photoresist pattern to expose a part of the material layer, and
etching an exposed part of the material layer,
wherein the hardmask composition includes:
a monomer represented by the following Chemical Formula 1, and
a solvent,

[Chemical Formula 1]

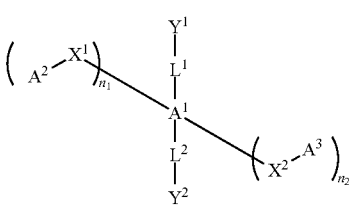

wherein, in Chemical Formula 1,
$A^1$ to $A^3$ are each independently a substituted or unsubstituted aliphatic cyclic group or aromatic cyclic group,
$X^1$ and $X^2$ are each independently C=O, $NR^a$, oxygen (O), sulfur (S), $CR^bR^c$, or a combination thereof, wherein $R^a$ to $R^c$ are each independently hydrogen, a substituted or unsubstituted C1 to C10 alkyl group, a hydroxy group, a halogen atom, a halogen-containing group, or a combination thereof,
$L^1$ and $L^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, or a combination thereof,
$Y^1$ and $Y^2$ are each independently a substituted or unsubstituted C2 to C20 alkenyl group,
n1 and n2 are integers of $0 \leq n1 \leq 10$ and $0 \leq n2 \leq 10$, and
n1 and n2 are not simultaneously 0.

13. The method of claim 12, wherein the hardmask composition is applied using a spin-on coating method.

* * * * *